United States Patent [19]

Kemp

[11] Patent Number: Plant 5,334

[45] Date of Patent: Nov. 13, 1984

[54] APPLE TREE 'TOP-SPUR'

[75] Inventor: Harry M. Kemp, Olympia, Wash.

[73] Assignee: C & O Nursery, Wenatchee, Wash.

[21] Appl. No.: 401,819

[22] Filed: Jul. 26, 1982

[51] Int. Cl.[3] ..... A01H 5/00

[52] U.S. Cl. ..... Plt./35

[58] Field of Search ..... Plt./35

[56] References Cited

U.S. PATENT DOCUMENTS

P.P. 2,606 3/1966 Cooper ..... Plt./35

P.P. 3,974 11/1976 Slusarenko ..... Plt./35

P.P. 4,587 8/1980 Perleberg ..... Plt./35

*Primary Examiner*—James R. Feyrer

*Attorney, Agent, or Firm*—Christensen, O'Connor, Johnson & Kindness

[57] ABSTRACT

A new and distinct variety of Red Delicious apple tree similar in most respects to Red Chief, but distinguishable therefrom (and from other generally similar varieties) in shape, skin coloration and flesh color characteristics of their fruit.

1 Drawing Figure

This discovery concerns a new and distinct cultivar apple tree occurring as a limb mutation on a Bisbee Delicious. Named Top-Spur, this sport limb originated in an orchard located in Farm Unit 162 of Irrigation Block 82, Columbia Basin Project, according to the plat thereof filed Sept. 2, 1958, records of Grant County, Washington.

The mutation sport limb was propagated by bud grafting on two trees, and wood from these was in turn bud grafted on 20 young trees. The unique and distinguishing characteristics of this new strain were maintained through the successive generations produced by such asexual reproduction.

The new variety nearest resembles Red Chief, U.S. Plant Pat. No. 3,578, itself a mutation of the same parent, Bisbee; in fact, the new variety appears to resemble Red Chief in virtually all respects except for the fruit as set forth below.

The accompanying photoprint is of a typical apple of the new variety.

TREE (COMPARED WITH RED CHIEF)

Form; The tree itself, very similar to if not substantially indistinguishable from Red Chief, is a spur-type, semi-dwarf. The growth on seedling stock is vigorous, with an upright and vase-shaped form. The branches are profuse with fruit spurs with short internodes, a growth pattern that makes the tree smaller than such Delicious trees as Topred. The trunk is smooth and stocky; the branches, thick and smooth and of the reddish-brown to gray color of Red Chief.

Leaf: Like Red Chief, the leaves are medium in length and width and of the same dark green color and thickness. They are abruptly pointed and rugose, with finely serrated margins.

Flowers: Again, like Red Chief, the flowers are white and of medium size. They generally bloom around the end of April in the Columbia Basin area of Washington State. Redspur is another Delicious tree that blooms at about the same time.

FRUIT (COMPARED WITH RED CHIEF)

Shape: The fruit of the new variety is more tapered from its transverse plane of maximum diameter to its calyx end than that of Red Chief. Its calyx cavity is much deeper; for example, in a size 80 apple, the depth of the calyx cavity between its base and the tips of the base end knobs of the apple will be on the average between ten millimeters and twelve millimeters, nearly twice the depth of Red Chief. Moreover, the knobs at the calyx end of the apple are much more prominent or separately protuberant than those on the fruit of Red Chief.

Skin: The skin appears similar to that of the fruit of Red Chief, except the stripes are more prominent at harvest time. Like Red Chief, the fruit skin is medium tough, smooth, and glossy. Its lenticels are medium and few in number. While there is very little difference in the appearance of the lenticels of the fruit of the two varieties, those of the present, new mutant appear to be somewhat more prominent than those of Red Chief from the middle of the apple to the calyx end. The color of the fruit, as identified by the Nickerson Color Fan of Munsell Color Company, is as follows: The darkest striping is a dark red, 5R3/7, with lighter red color ranging from strong red, 5R4/12 to 5R5/13. Coloration starts about five weeks before maturity and initially exhibits a very strong striped configuration. By the time of maturity, the striping has been largely masked in a bright red overall coloration as previously indicated.

Flesh: The flesh is whiter than the flesh of Red Chief. It is a creamy white. The flesh is juicy, firm, and crisp. The vascular bundles are white and the core is symmetrical. The seed cells are open with an average length of ¾ of an inch. Like Red Chief, the flesh matures earlier than that of either Redspur or Topred, based comparatively on soluble solids and flesh color. The fruit matures, as does that of Red Chief, by some five to seven days earlier than Bisbee in the Columbia Basin area.

Seeds: The formation of seeds is quite consistently and essentially perfect, with a full complement of ten in most apples, subject to alteration by injurious weather patterns.

Pedicel: The pedicel is medium thick and its color is predominately striped red, developing early in the growing season with the stripes running the full length of the apple, as with Red Chief.

Use: The apple is primarily a dessert apple having excellent eating properties and excellent storage life (i.e., approximately 160 days when kept under industry standard commercial refrigeration).

FRUIT (COMPARED WITH OTHER NEAR RELATED VARIETIES)

Top-Spur fruit compares with that of Starkrimson (Bisbee) as follows: Having substantially the same diameter (about 8.5 centimeters), the Top-Spur apple is longer than that of Starkrimson by about 1.0 centimeter, the former averaging 9.0 centimeters and the latter 8.0 centimeters, yielding a length-to-diameter ratio of 1.06 centimeters for the Top-Spur apple and 0.94 for the Starkrimson apple. The calyx depth of Top-Spur is typically 2.0 centimeters and that of Starkrimson is 1.5 centimeters. Top-Spur is a deep red color compared to the pale red of Starkrimson and has a definite but moderate stripe, whereas Starkrimson shows a solid color. Flesh of Top-Spur is solid white compared with the white with a green tint in Starkrimson. Top-Spur fruit is at least two weeks earlier to mature than Starkrimson.

Top-Spur fruit compares with that of Ace and Wellspur (referencing here, without repeating, the relevant Top-Spur fruit characteristics described just above) as follows:

Ace averages a diameter of 7.9 centimeters, a length of 8.1 centimeters, with a length-to-diameter ratio of 1.02.

Wellspur averages a diameter of 7.8 centimeters, a length of 8.5 centimeters and a length-to-diameter ratio of 1.08.

Both Ace and Wellspur have calyx cavities averaging about 1.0 centimeters deep, approximately half that of Top-Spur.

Colorwise, Ace is deep red with a moderate pale strip, whereas Wellspur is a solid red color.

In terms of flesh color, Ace has white flesh with green vessel ends. Wellspur has pale green flesh.

I claim:

1. The new and distinct variety of Red Delicious apple tree substantially as shown and described, characterized in particular in the shape and coloration of its fruit both as to skin and flesh, referring to Red Chief as the principal basis of comparison in view of its similarity to Red Chief in most other respects and also, secondarily to Starkrimson, Ace and Wellspur.

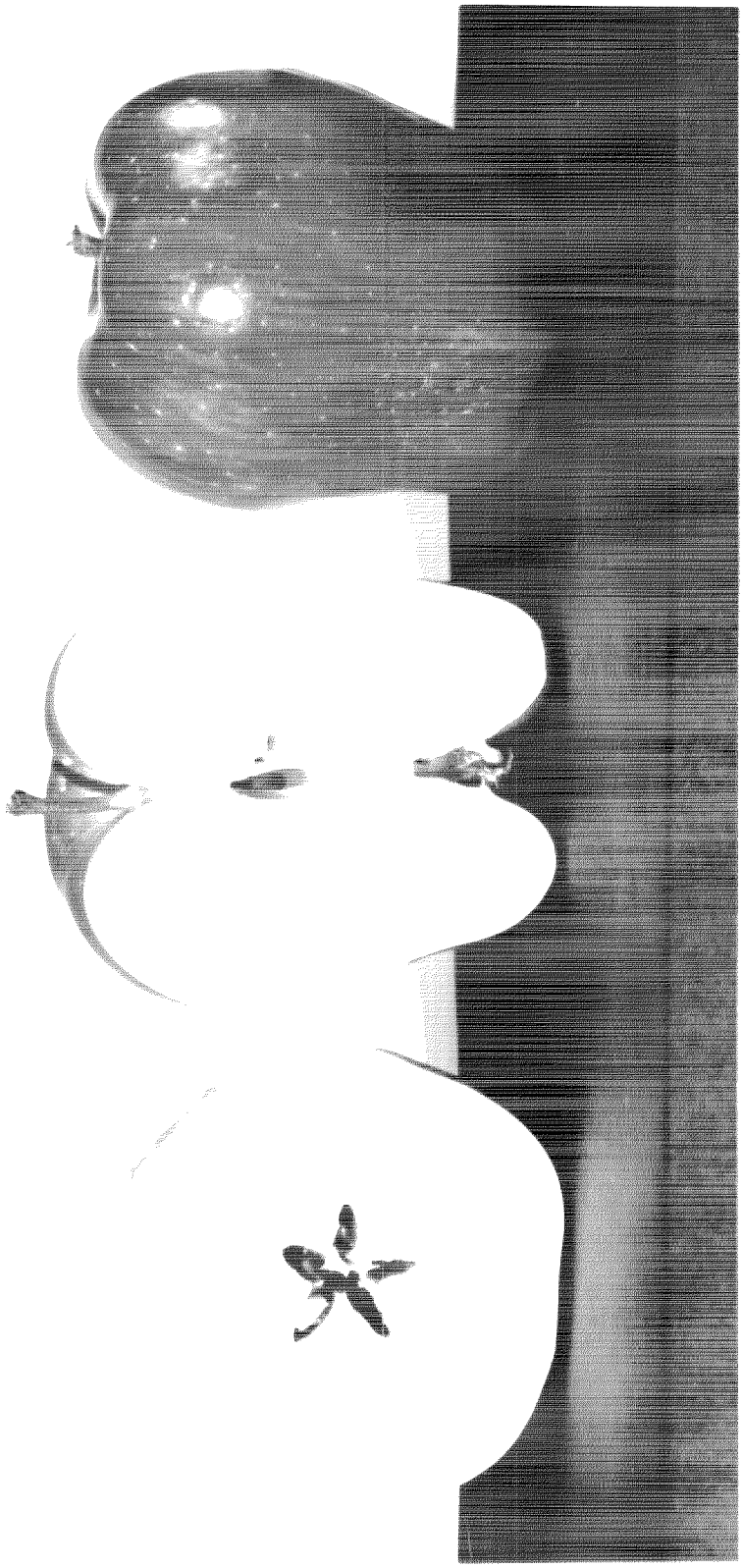

* * * * *